United States Patent
Itou et al.

(10) Patent No.: US 11,080,825 B2
(45) Date of Patent: Aug. 3, 2021

(54) MAGNETIC RESONANCE IMAGING APPARATUS AND IMAGE PROCESSING METHOD

(71) Applicant: Hitachi, Ltd., Tokyo (JP)

(72) Inventors: Kousuke Itou, Tokyo (JP); Shinji Kurokawa, Tokyo (JP); Masahiro Takizawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/629,479

(22) PCT Filed: Jul. 5, 2018

(86) PCT No.: PCT/JP2018/025583
§ 371 (c)(1),
(2) Date: Jan. 8, 2020

(87) PCT Pub. No.: WO2019/039112
PCT Pub. Date: Feb. 28, 2019

(65) Prior Publication Data
US 2020/0126188 A1    Apr. 23, 2020

(30) Foreign Application Priority Data
Aug. 25, 2017   (JP) .............................. JP2017-162615

(51) Int. Cl.
*G06T 3/40* (2006.01)
*G06T 7/00* (2017.01)
(Continued)

(52) U.S. Cl.
CPC .......... *G06T 3/4053* (2013.01); *G06T 7/0002* (2013.01); *G06T 2207/10088* (2013.01); *G06T 2207/20182* (2013.01)

(58) Field of Classification Search
None
See application file for complete search history.

(56) References Cited

U.S. PATENT DOCUMENTS

| | | |
|---|---|---|
| 5,345,172 A | 9/1994 | Taguchi |
| 2003/0001571 A1 | 1/2003 | Wang |

(Continued)

FOREIGN PATENT DOCUMENTS

| | | |
|---|---|---|
| JP | H04-357935 A | 12/1992 |
| JP | 2004-154401 A | 6/2004 |

(Continued)

OTHER PUBLICATIONS

International Search Report with English translation and Written Opinion issued in corresponding application No. PCT/JP2018/025583 dated Sep. 18, 2018.

(Continued)

*Primary Examiner* — Mohammed Rachedine
(74) *Attorney, Agent, or Firm* — Foley & Lardner LLP

(57) ABSTRACT

Provided is a novel aliasing elimination technique capable of suppressing noise amplification in an aliasing elimination calculation in parallel imaging and the like. The technique utilizes the fact that a phase of an image (a true image that is one of a plurality of images) to be separated from a main captured image obtained with the plurality of images superimposed is basically the same as a phase of an image obtained at a low resolution, to obtain a phase difference between a phase of a low-resolution image and a phase of the main captured image, and separates the true image by calculation using the phase difference and a pixel value of the main captured image. At this time, the low-resolution image is obtained by each of a plurality of receiving coils, and the true image is calculated after multiplying a plurality of low-resolution images by a complex number that minimizes the noise amplification.

11 Claims, 12 Drawing Sheets

(51) Int. Cl.
*G06T 5/00* (2006.01)
*G01R 33/483* (2006.01)
*G01R 33/561* (2006.01)
*A61B 5/055* (2006.01)

(56) References Cited

U.S. PATENT DOCUMENTS

| | | | | |
|---|---|---|---|---|
| 2009/0180155 | A1* | 7/2009 | Kato | H04N 1/3873 |
| | | | | 358/448 |
| 2009/0316218 | A1* | 12/2009 | Miyagi | H04N 1/40062 |
| | | | | 358/448 |
| 2010/0103474 | A1* | 4/2010 | Oiwa | H04N 1/00737 |
| | | | | 358/461 |
| 2014/0086085 | A1* | 3/2014 | Zheng | H04L 5/0092 |
| | | | | 370/252 |
| 2014/0219533 | A1 | 8/2014 | Sato | |
| 2016/0165545 | A1* | 6/2016 | Ouchi | H04W 52/228 |
| | | | | 455/522 |
| 2016/0165547 | A1* | 6/2016 | Ouchi | H04W 52/146 |
| | | | | 455/522 |
| 2017/0097399 | A1 | 4/2017 | Shiodera | |
| 2019/0372697 | A1* | 12/2019 | Wang | H04L 1/0056 |
| 2020/0059286 | A1* | 2/2020 | Xiong | H04B 7/0857 |

FOREIGN PATENT DOCUMENTS

| | | | |
|---|---|---|---|
| JP | 2008-006117 A | 1/2008 | |
| JP | 2010-233907 A | 10/2010 | |
| JP | 2017-070386 A | 4/2017 | |
| WO | WO-2010131436 A1 * | 11/2010 | G03B 13/20 |
| WO | WO-2013/054718 A1 | 4/2013 | |
| WO | WO-2015126060 A1 * | 8/2015 | H04N 5/23222 |

OTHER PUBLICATIONS

Pruessmann et al., "SENSE: Sensitivity Encoding for Fast MRI", Magnetic Resonance in Medicine 42, 1999, pp. 952-962.

Breuer et al., Controlled Aliasing in Volumetric Parallel Imaging (2D CAIPIRINHA), Magnetic Resonance in Medicine 55, 2006, pp. 549-556.

International Preliminary Report on Patentability issued in corresponding International Application No. PCT/JP2018/025583 dated Mar. 5, 2020.

* cited by examiner

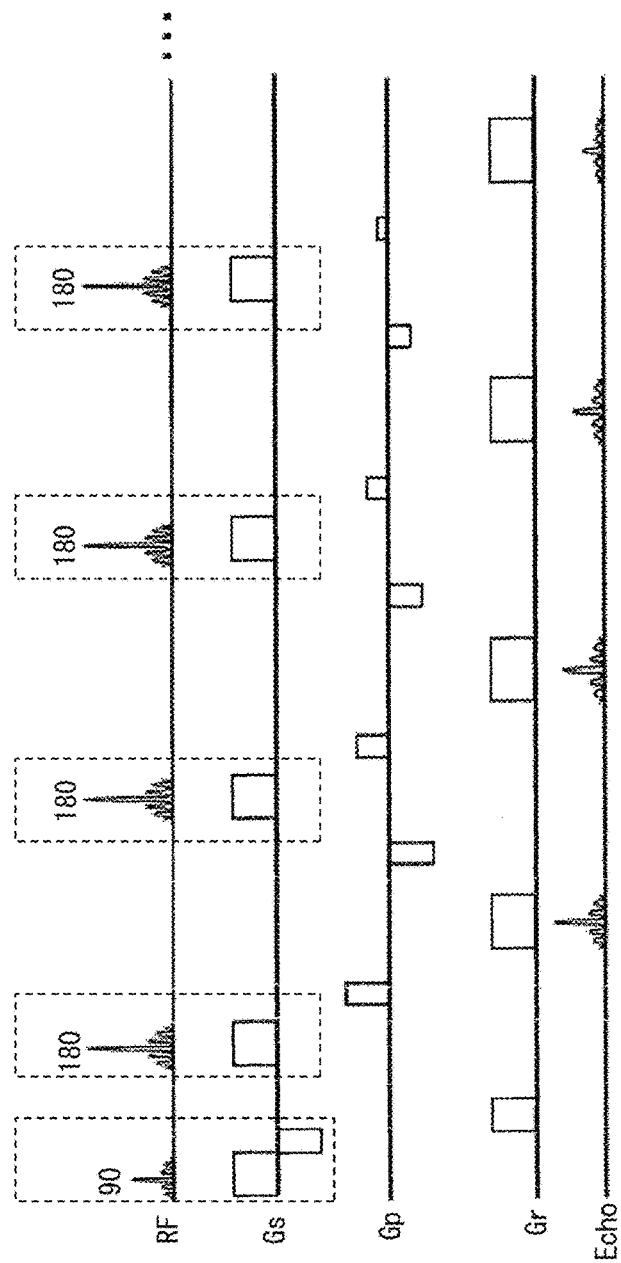
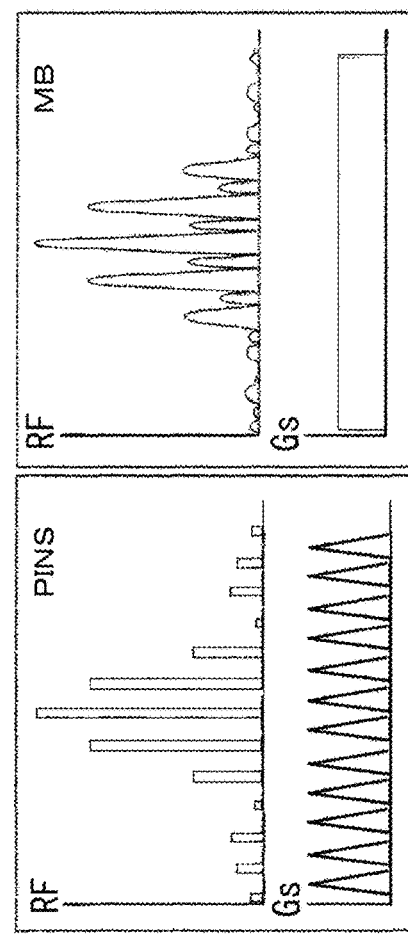
Fig. 7A
Fig. 7B
Fig. 7C

MAIN CAPTURED IMAGE R

IMAGE S1 OF slice 1

IMAGE S2 OF slice 2

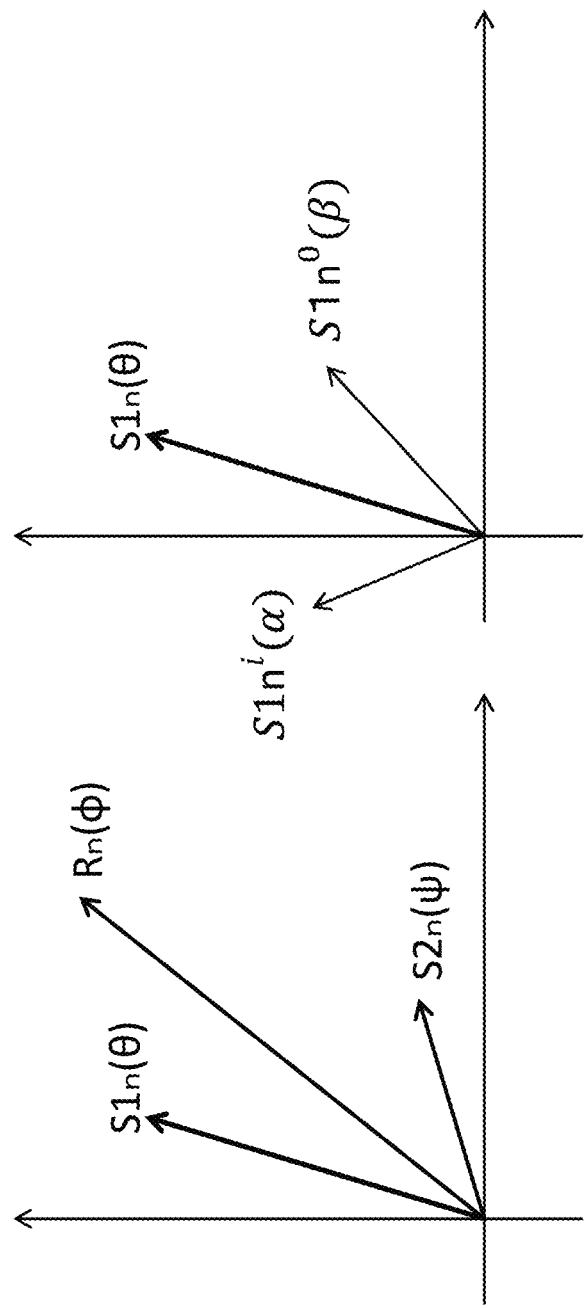

SIMULTANEOUS EXCITATION

INDIVIDUAL EXCITATION

AFTER SEPARATION

DIFFERENCE

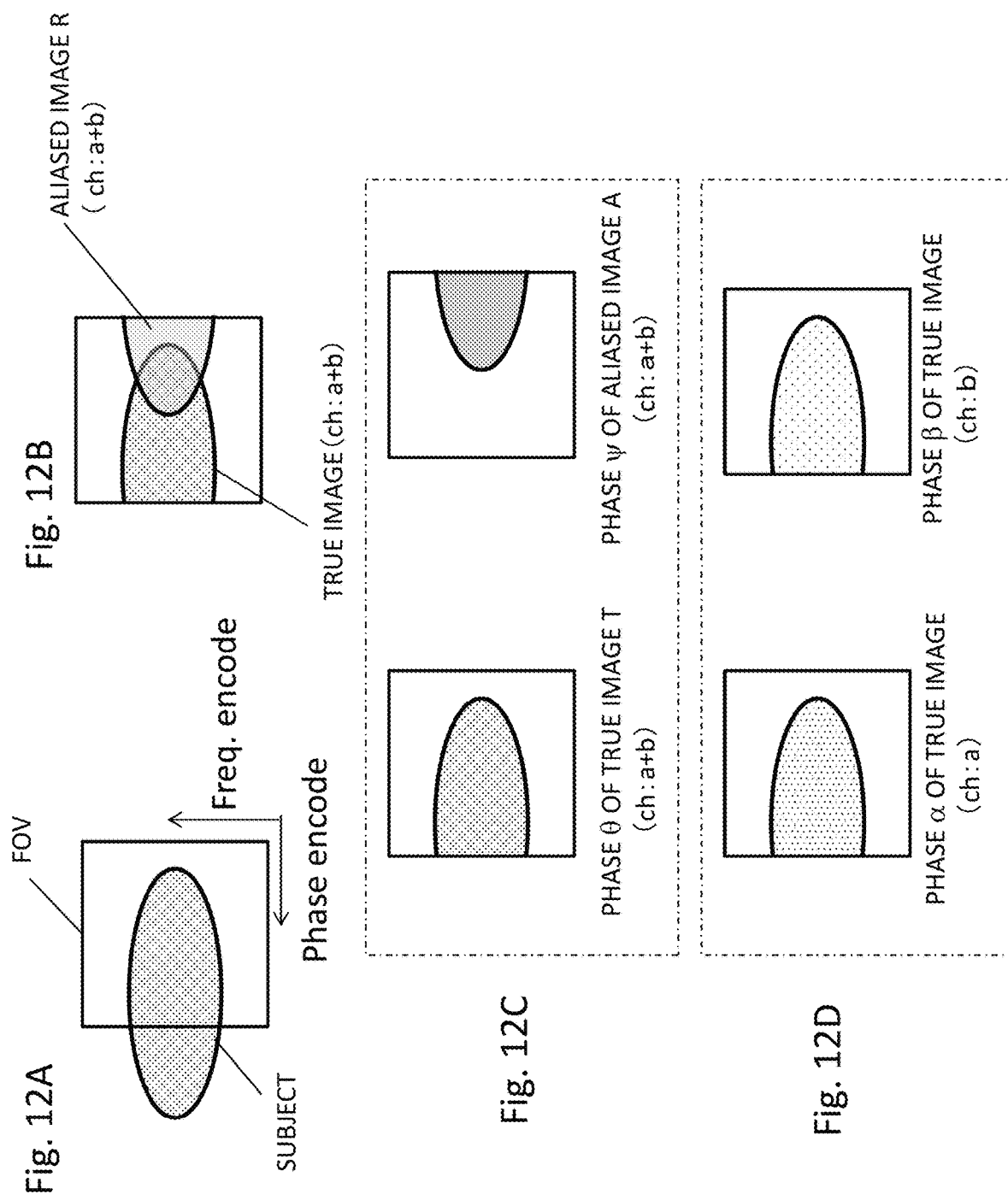

MAGNETIC RESONANCE IMAGING APPARATUS AND IMAGE PROCESSING METHOD

TECHNICAL FIELD

The present invention relates to a technique for eliminating aliasing of an image or separating superimposed images in a magnetic resonance imaging apparatus (hereinafter referred to as an MRI apparatus).

BACKGROUND ART

The MRI apparatus is an imaging apparatus for obtaining the image from a signal obtained by a magnetic resonance phenomenon of predetermined nuclear spins in a subject tissue, and phase encoding in one or two directions is given to a nuclear magnetic resonance signal by gradient magnetic field pulses for imaging. In the MRI apparatus, it is necessary to repeat measurement of the nuclear magnetic resonance signal in order to give phase encoding, and there is a problem that a measurement time is prolonged.

Various techniques for shortening the measurement time have been proposed, and one of them is parallel imaging in which k-space data is reduced and measured. When the k-space data is undersampled in a phase encoding direction, the aliasing (wrap-around) occurs in the image. In parallel imaging, sensitivity distribution of a plurality of receiving coils is used to eliminate aliasing of the image caused by undersampling. There are two major methods for unfolding wraparound, one is a method of unfolding aliasing by calculation of measurement domain (SMASH method, GRAPPA), and the other is a method of eliminating aliasing by calculation of an image domain (SENSE method) (Non-Patent Literature 1).

In these parallel imaging techniques, an image quality is greatly affected by g factor determined by shapes and spatial arrangement of the receiving coils. Although the g factor should ideally be 1, there is a limit to forming ideal receiving coil configuration in all imaging. In image reconstruction of parallel imaging depending on the sensitivity distribution, SNR degradation of about g factor occurs. It has also been proposed to devise the data-reduction method in order to reduce the g factor (Non-Patent Literature 2).

CITATION LIST

Non-Patent Literature

Non-Patent Literature 1: Klaas P. Pruessmann, et al Magnetic Resonance in Medicine 42: 952-962(1999), "SENSE: Sensitivity Encoding for Fast MRI"

Non-Patent Literature 2: Felix A. Breuer, et al Magnetic Resonance in Medicine 55: 549-556(2006) "Controlled Aliasing in Volumetric Parallel Imaging"

SUMMARY OF THE INVENTION

Technical Problem

The data-reduction method proposed by Non-Patent Literature 2 can be applied to three-dimensional k-space data, but is difficult to be applied to 2D data. Also in this technique, noise amplification due to the g-factor and the undersampled acquisition still occurs. In particular, the noise amplification due to the g factor determined by independence of sensitivity for each channel of the receiving coil is inevitable. Therefore, if an acceleration factor (reduction rate) is set high such that an aliased portion is generated near a position of a true image, degradation of the SNR is inevitable.

Unlike a conventional technique that eliminates aliasing using the sensitivity distribution of the receiving coil, an object of the present invention is to provide a new technique for eliminating aliasing using a phase of the image, to suppress the noise amplification.

Means for Solving the Problems

In order to achieve the above object, the present invention utilizes the fact that the phase of the image (a true image that is one of a plurality of images) to be separated from a main captured image obtained in a state where the plurality of images are overlapped (superimposed) is basically the same as a phase of an image obtained at a low resolution, to obtain a phase difference between a phase of a low-resolution image and a phase of the main captured image, and separates the true image by calculation using the phase difference, and a pixel value of the main captured image. At this time, the low-resolution image is obtained by each of the plurality of receiving coils, and the true image is calculated after multiplying a plurality of low-resolution images by a complex number that minimizes the noise amplification.

That is, an MRI apparatus of the present invention includes: an imaging unit having a plurality of receiving coils and collecting nuclear magnetic resonance signals from a subject; and an image processing unit for reconstructing an image of the subject using the nuclear magnetic resonance signals collected by the imaging unit. The image processing unit includes an image separation unit for using a phase of a low-resolution image reconstructed from the nuclear magnetic resonance signals obtained by each of the plurality of receiving coils, and a phase of a main captured image that is reconstructed from the nuclear magnetic resonance signals obtained by the plurality of receiving coils, and superimposed with a plurality of images, to separate the plurality of images included in the main captured image.

Advantage of the Invention

According to the present invention, since images can be separated without using the sensitivity distribution of the receiving coils, the noise amplification due to the g factor can be suppressed. In particular, by using the phases of the plurality of low-resolution images obtained from the plurality of receiving coils, it is possible to suppress noise of the image obtained by imaging from being amplified by image processing, thereby obtaining the image having a good SNR. The present invention can be applied not only to processing of the image including aliasing obtained by so-called parallel imaging (undersampling measurement), but also to images of multiple excitation cross-sections and images including aliasing artifacts of subject images other than FOV.

BRIEF DESCRIPTION OF THE DRAWINGS

FIGS. 7A to 7C are diagrams showing an example of a pulse sequence used in a second embodiment, FIG. 7A is an SMS pulse sequence diagram, and FIGS. 7B and 7C are diagrams showing examples of SMS RF pulses.

FIGS. 9A and 9B are diagrams showing a relationship between phases of the captured image and cross-sectional images in the second embodiment.

FIGS. 12A to 12D are diagrams illustrating the captured image and aliasing in a third embodiment.

MODE FOR CARRYING OUT THE INVENTION

Embodiments of an MRI apparatus of the present invention will be described below with reference to the drawings.
<Configuration of Apparatus>

First, configuration of an apparatus common to the embodiments described below will be described.

Figure 1:
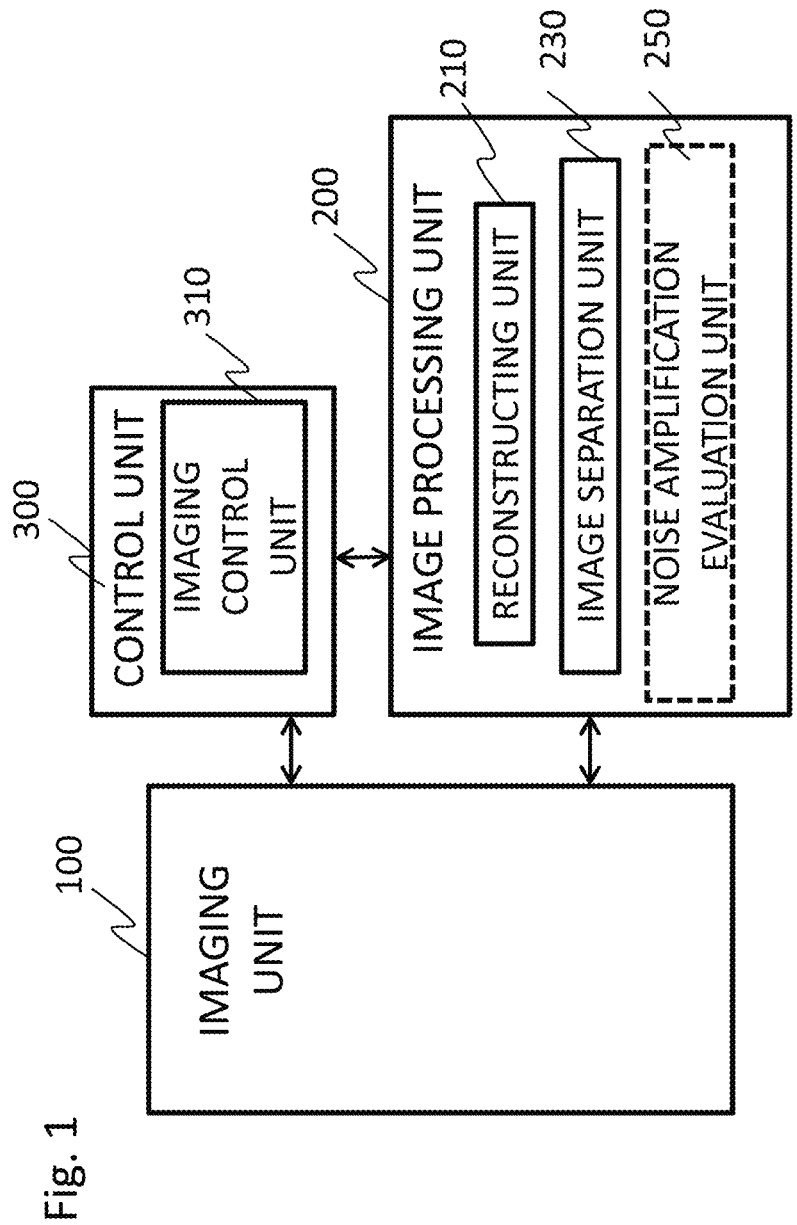
FIG. 1 is a diagram showing an overall configuration of an MRI apparatus.

FIG. 1 shows an overall configuration of the MRI apparatus to which the present invention is applied. This MRI apparatus mainly includes an imaging unit 100, an image processing unit 200, and a control unit 300.

Figure 2:
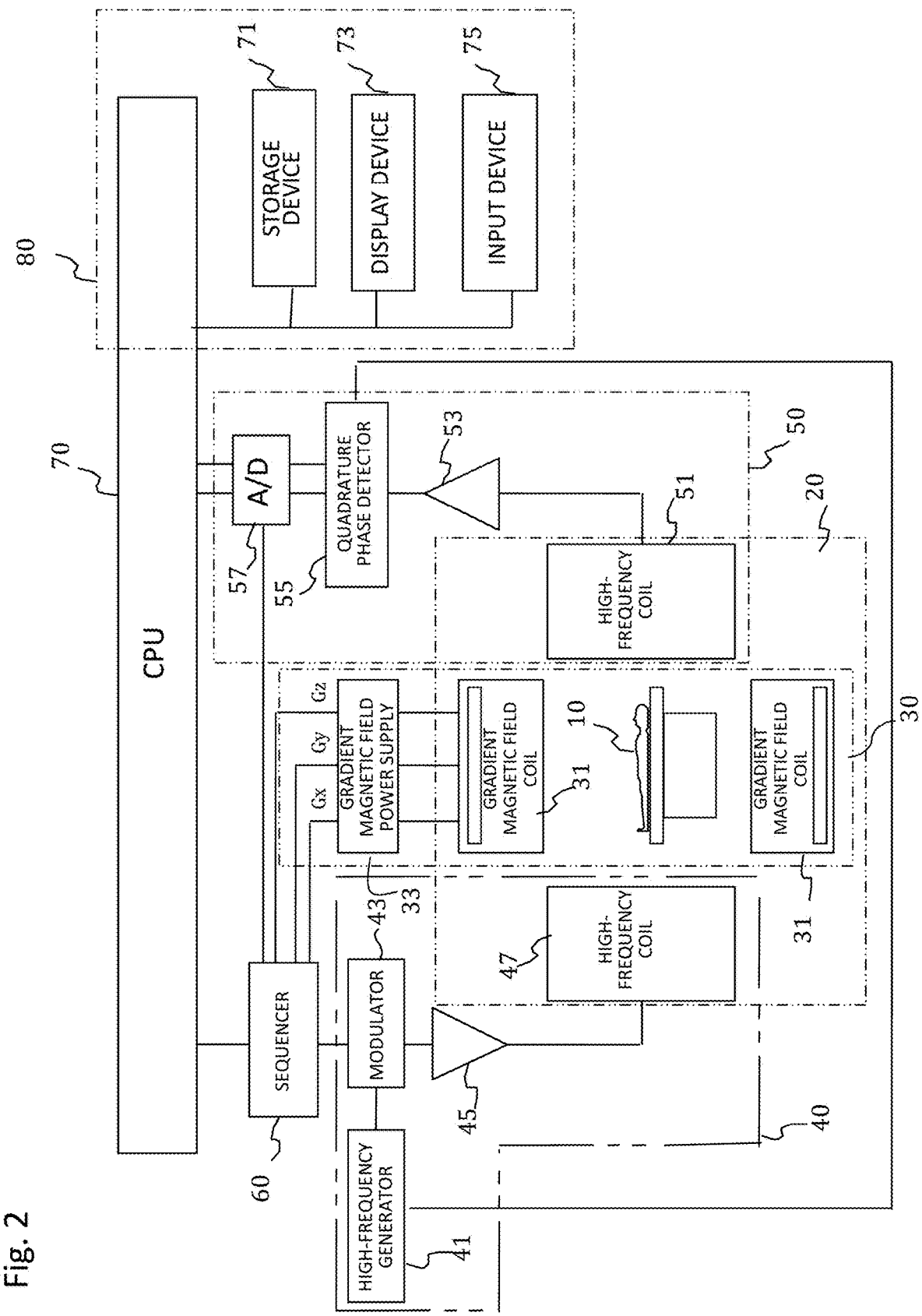
FIG. 2 is an overall configuration diagram of the MRI apparatus including details of an imaging unit.

The imaging unit 100 is a unit for generating nuclear magnetic resonance in nuclear spins of atoms constituting a tissue of a subject, and as a result, collecting nuclear magnetic resonance signals generated by the nuclear spins, and has a similar configuration to a known MRI apparatus. Specifically, as shown in FIG. 2, the imaging unit 100 includes: a static magnetic field generating unit 20 for generating a static magnetic field in a space where a subject 10 is placed; a gradient magnetic field generating unit 30 for applying a magnetic field gradient to a static magnetic field space; a transmitting unit 40 for generating a high-frequency magnetic field that generates magnetic resonance in the nuclear spins of the nuclei constituting the tissue of the subject 10; a receiving unit 50 for receiving the nuclear magnetic resonance signals generated from the subject 10 (nuclear spin) in response to the high-frequency magnetic field from the transmitting unit 40; and a sequencer 60 for operating the gradient magnetic field generating unit 30, the transmitting unit 40, and the receiving unit 50 according to a predetermined pulse sequence.

The static magnetic field generating unit 20 includes a static magnetic field generator such as a superconducting magnet, a normal conducting magnet, or a permanent magnet. There are a vertical magnetic field method and a horizontal magnetic field method depending on direction of the static magnetic field, whichever may be employed.

The gradient magnetic field generating unit 30 includes three sets of gradient magnetic field coils 31 for generating gradient magnetic fields in three axial directions (x, y, z) orthogonal to each other, and a gradient magnetic field power supply 33 for driving each gradient magnetic field coil 31. The magnetic field gradient can be formed in an arbitrary direction by combining the gradient magnetic fields of the respective axes, which gives position information to the nuclear magnetic resonance signals.

The transmitting unit 40 includes a high-frequency generator 41, a modulator 43, an amplifier 45, and a transmitting high-frequency coil (transmitting RF coil) 47. The receiving unit 50 includes a receiving high-frequency coil (referred to as a receiving probe) 51, an amplifier 53, a quadrature phase detector 55, and an A/D converter 57. The reception probe 51 is a combination of a plurality of receiving RF coils, and includes the amplifier 53, the quadrature phase detector 55, and the A/D converter 57 for each receiving RF coil. That is, each receiving RF coil constitutes each channel of the receiving probe, and an output is obtained for each receiving RF coil constituting the receiving probe, that is, for each channel.

The transmitting RF coil 47 and the receiving probe 51 are arranged close to the subject 10 and apply the high-frequency magnetic field and detect the nuclear magnetic resonance signals. In the figure, the transmitting RF coil 47 and the receiving probe 51 are shown as separate ones, but one coil may serve as both for transmission and reception.

The image processing unit 200 and the control unit 300 are implemented as software in CPU 70. However, some functions of the image processing unit 200 may be implemented by hardware such as ASIC (Application Specific Integrated Circuit) or FPGA (Field Programmable Gate Array). In addition to the image processing unit 200 and the control unit 300, the MRI apparatus includes: a storage device (including a memory in the CPU) 71 for storing information necessary for operations of the units, processing results of the image processing unit, and the like; a display device 73 for displaying processing results and the like; and an input device 75 for inputting conditions, numerical values and the like necessary for the operations of the units. The display device 73 and the input device 75 may be arranged close to each other, to function as a user interface unit 80.

The control unit 300 controls the operation of the imaging unit 100 via the sequencer 60 (an imaging control unit 310), and controls the operation of the image processing unit 200 and display of the display device 73. The imaging control unit 310 passes parameters of a predetermined pulse sequence selected from various pre-programmed pulse sequences depending on an imaging purpose and a pulse sequence input via the input device 75 to the sequencer 60, to control imaging.

The image processing unit 200 is a unit for processing the nuclear magnetic resonance signal collected by the imaging unit 100 to image a desired site or tissue of the subject, and includes a reconstructing unit 210 for performing operations such as Fourier transform on k-space data including nuclear magnetic resonance signals to generate image data, and an image separation unit 230 for performing operations such as aliasing elimination using phase information, on the image data generated by the reconstructing unit 210. The image separation unit 230 preferably includes a noise amplification evaluation unit 250 for evaluating noise amplification in order to optimize the noise amplification in an image separation process.

The pulse sequence used in the MRI apparatus includes various pulse sequences that differ depending on the imaging purpose and the like, and can be roughly divided into a spin echo (SE) pulse sequence and a gradient echo (GrE) pulse sequence. In either case, the nuclear magnetic resonance signals collected by its execution is phase-encoded by gradient magnetic field pulses of each axis, and data sampled from them is arranged in k-space having axes in a readout gradient magnetic field direction and a phase encoding gradient magnetic field direction. A size of the k-space is determined by a relationship with FOV (field of view), and the k-space data is usually sampled so as not to include signals from outside the field of view. However, in order to increase speed, there are also imaging that undersamples the k-space data and imaging that excites a plurality of slices simultaneously, to collect signals from the plurality of slices at the same time. In the former case, the k-space data is data including aliasing of an image, and in the latter case, the k-space data is data in which the image data of the plurality of slices is superimposed (overlapped). Ordinarily, when the signal from the subject that is oversampled and to be removed is out of the field of view, even when imaging is performed without oversampling, the k-space data is the data including aliasing.

When the k-space data collected initially in this manner includes a plurality of image data, the image separation unit 230 of the image processing unit 200 separates the image data under a condition that does not cause aliasing or by using the phase information of the low-resolution image obtained from only one slice. Hereinafter, the principle of image separation using phase performed by the image separation unit 230 will be described. In the image separation using the phase, it is basically assumed that phase change in an image space of a complex image is gentle. Therefore, it is preferred that the pulse sequence is the SE pulse sequence that is not easily affected by non-uniform static magnetic field distribution.

<Principle of Image Separation>

Figure 3:
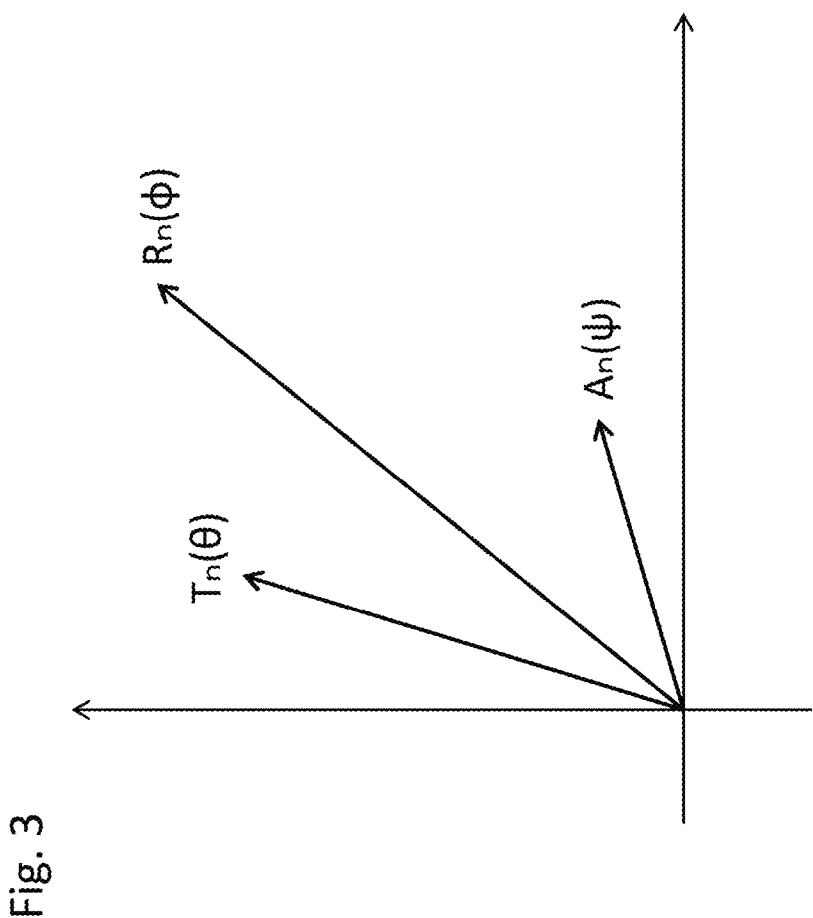
FIG. 3 is an explanatory diagram showing a relationship between phases of a captured image and a true image.

The image of MRI obtained by Fourier transforming the k-space data is the complex image, and a value (signal) of each pixel is a complex number represented by an absolute value (a signal intensity) and the phase. Now, assuming that the complex number of one point (one pixel) of a captured image R including aliasing is $R_n(\varphi)$, $R_n(\varphi)$ is represented by a vector sum of a signal $T_n(\theta)$ of a true image T and a signal $A_n(\psi)$ of an aliased image A (where $\varphi$, $\theta$, and $\psi$ are the phases of the respective signals (complex numbers)) as shown in FIG. 3. That is, a diagonal of a parallelogram formed by the signal $T_n$ and the signal $A_n$ is $R_n$. From this relationship, the signal intensity (absolute value of $T_n$) of the true image is expressed by the following equation using $R_n$, $\varphi$, $\theta$, and $\psi$. Note that a subscript "n" of $R_n$, $T_n$, and $A_n$ is a symbol for indicating that $R_n$, $T_n$, and $A_n$ are respectively pixels of points included in the images R, T, and A.

[Equation 1]

$$|Tn| = |Rn| \times \left| \frac{\sin(\phi - \Psi)}{\sin(\theta - \psi)} \right| \quad (1)$$

Therefore, if the phase ($\varphi$, $\theta$, $\psi$) of each signal is known, the true image T (complex number of each pixel) can be separated from these phases and the image R (complex number of each pixel) including aliasing. Here, "$\varphi$" can be obtained by Fourier transforming data of a central portion of the captured image R, and "$\theta$" is obtained by obtaining the image (low-resolution image) without aliasing in advance and Fourier transforming data of a central portion of the image. Further, since an amount of deviation from $\theta$ is determined depending on a reduction rate, "$\psi$" can be obtained from the amount of deviation if the reduction rate is known.

In this way, the true image can theoretically be separated from the captured image by the equation (1) if the phase is known. On the other hand, considering an effect of noise $\delta R$ included in the image R including aliasing on a size of the true image T, the noise amplification can be evaluated by the following equation (2) using the law of error propagation.

[Equation 2]

$$(\delta T)^2 = \frac{1}{\sin^2(\theta - \phi)}(\delta R)^2 \quad (2)$$

As can be seen from the equation (2), the noise $\delta R$ included in the image R is $1/\sin(\theta - \varphi)$ times. The noise is not easily amplified as a phase difference ($\theta - \varphi$) between the true image T and an aliasing A is closer to an odd multiple of 90°. That is, the noise amplification is minimized. Here, the phase difference ($\theta - \varphi$) between the true image T and the image R is a value determined by parameters of the apparatus and the pulse sequence, and is difficult to be adjusted. In the present embodiment, the noise amplification is further minimized by using the phases of the low-resolution images respectively received by the plurality of receiving coils. Hereinafter, a method for separating the true image and minimizing the noise amplification using the phase information will be described in detail in the embodiments having different imaging methods.

First Embodiment

Figure 4:
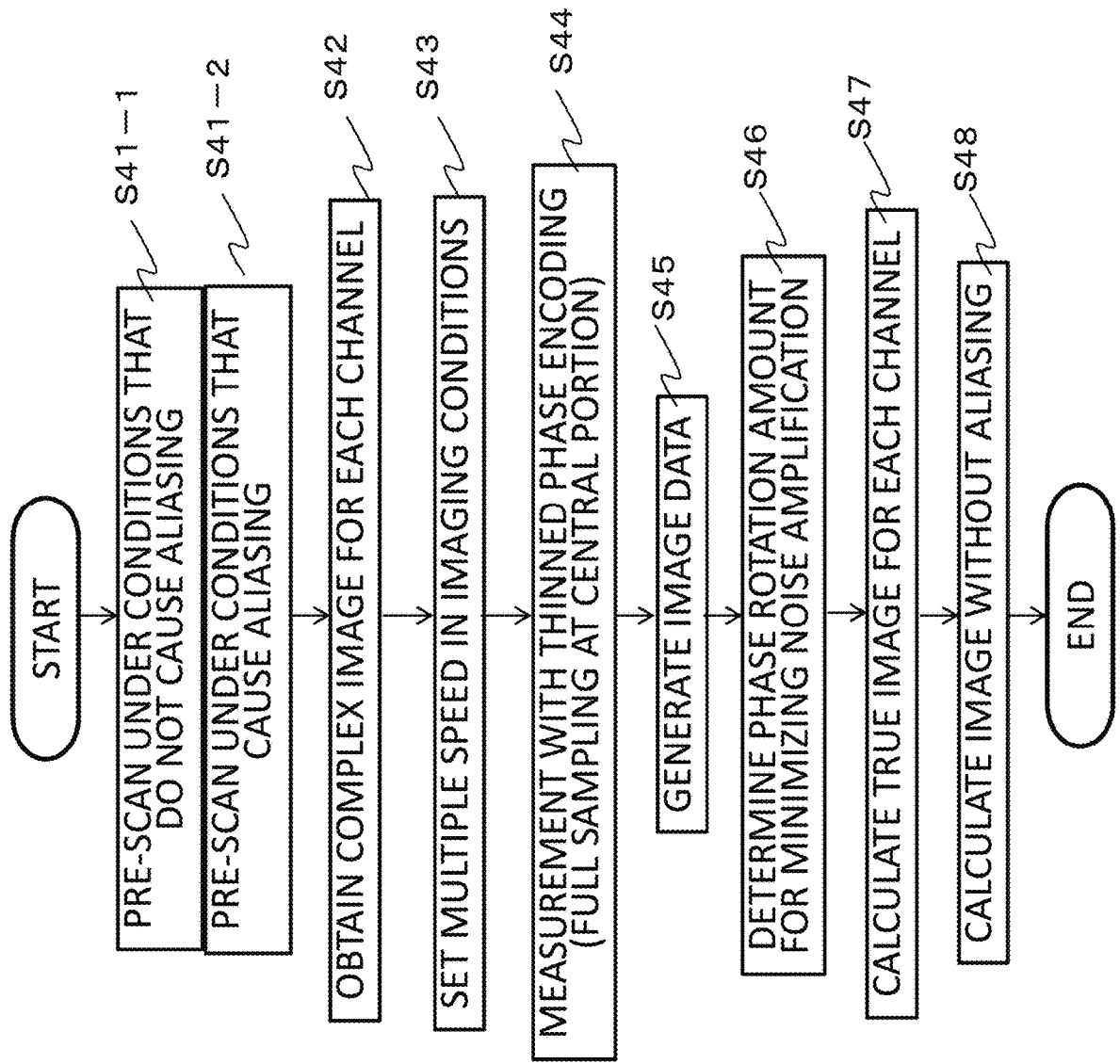
FIG. 4 is a flowchart showing processing by an image processing unit of a first embodiment.

In the present embodiment, the imaging unit 100 obtains the k-space data that is under-sampled at a predetermined reduction rate. The k-space data includes aliasing in a phase encoding direction. Hereinafter, an operation of the MRI apparatus of the present embodiment will be described with reference to a flowchart of FIG. 4 by taking as an example a case of obtaining 2D k-space data.

The imaging unit 100 performs two pre-scans under control of the control unit 300 (S41). In one pre-scan, the subject is pre-scanned under imaging conditions that do not cause aliasing, and the k-space data of a plurality of channels constituting the receiving probe 51 is collected (S41-1). In the other pre-scan, the pre-scan is performed at the same reduction rate as main imaging, and the k-space data of the plurality of channels is collected (S41-2). The pulse sequence of these pre-scans is not particularly limited, but for example, the SE pulse sequence such as FSE (Fast Spin Echo: see FIG. 7A) may be used. The reconstructing unit 210 obtains the phases $\theta$ and $\varphi$ of the image that is obtained by performing complex addition on the central portion of the k-space data for each channel for each pre-scan data, and then Fourier transforming the data (S42). The phase $\theta$ is the phase of the image obtained by the pre-scan under the imaging conditions that do not cause aliasing, and the phase $\varphi$ is the phase of the image obtained by the pre-scan of undersampled imaging.

Figure 5:
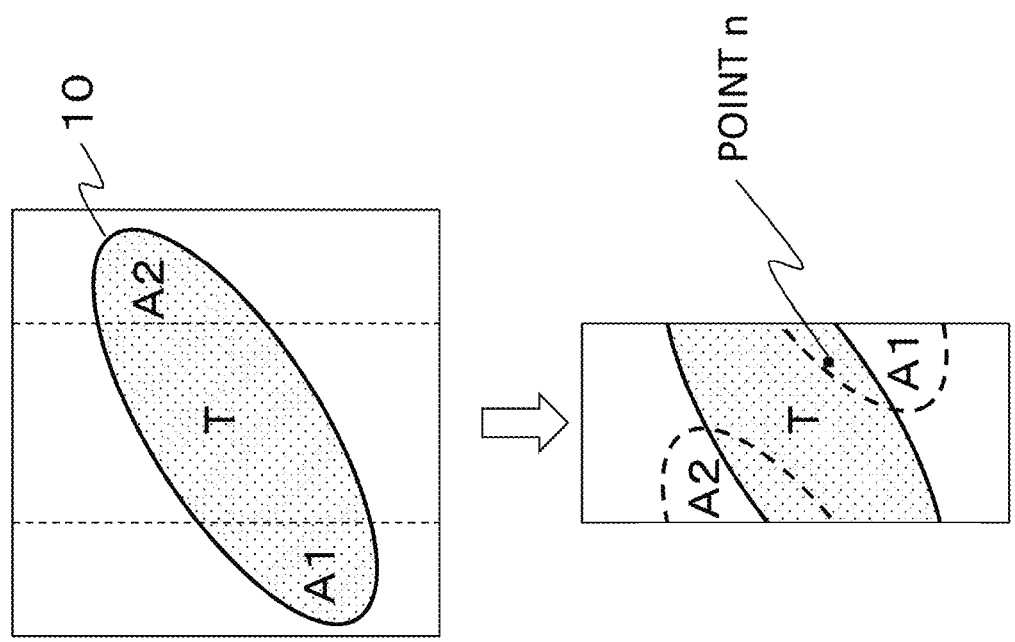
FIG. 5 is a diagram illustrating the captured image and an aliased image in the first embodiment.

Next, the control unit 300 sets the SE pulse sequence and the predetermined reduction rate (S43), and starts main imaging by the imaging unit 100 (S44). In the main imaging, the k-space data output from the plurality of channels is synthesized to create one k-space data. The reconstructing unit 210 Fourier transforms the k-space data, to generate the image data (S45). This is called a main captured image. The main captured image is the image including aliasing corresponding to the reduction rate. For example, when the reduction rate is ½, the image in which the image A (A1, A2) is aliased on the image T is obtained as shown in FIG. 5. In the following description, A1 and A2 are collectively described as the image A unless it is necessary to distinguish between them.

The image separation unit 230 separates the image T and the image A using the phases θ and φ of the low-resolution image obtained in Step S42 and the signal intensity of the main captured image R (S46 to S48). Hereinafter, the image separation process will be described in detail.

Figure 6:
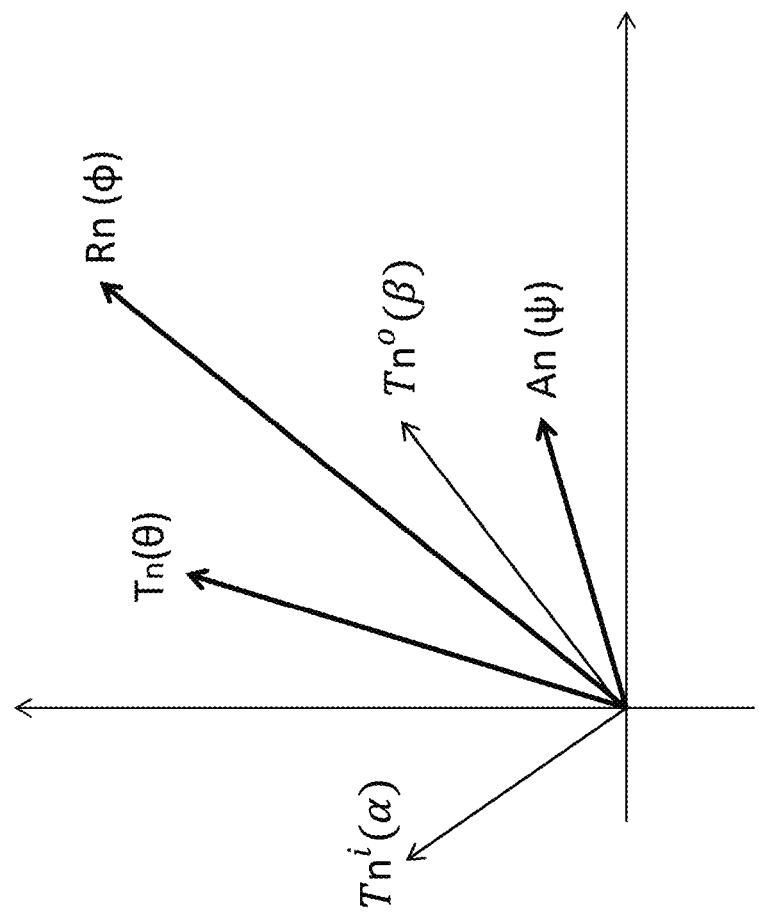
FIG. 6 is a diagram illustrating a relationship between phases of the captured image, a low-resolution image, and the aliased image in the first embodiment.
Figure 8A:
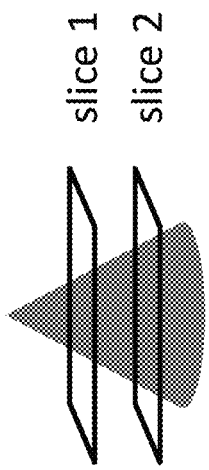
FIG. 8A is a diagram for explaining simultaneous excitation of different cross-sections in the second embodiment.
Figure 8B:
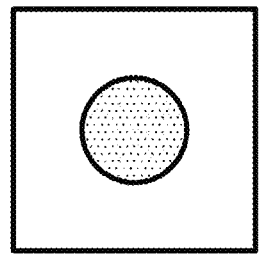
FIG. 8B is the captured image at the time of simultaneous excitation.
Figure 8C:
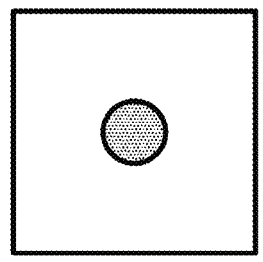
FIGS. 8C and 8D are diagrams showing images of different cross-sections.
Figure 8D:
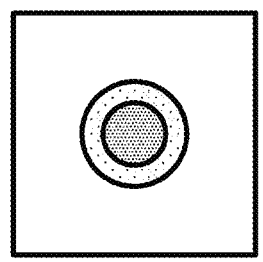

For the image T, the image A, and the main captured image R, when a signal at one point (for example, a point n in FIG. 5) on the image is shown on a complex plane, it can be represented by a complex number (vector) as shown in FIG. 6. The complex numbers indicated by thick arrows have the same relationship as T, A, and R shown in FIG. 3. Therefore, the image T is represented by the equation (1), and the image A is represented by the following equation (3).

[Equation 3]

$$|An| = |Rn| \times \left| \frac{\sin(\phi - \theta)}{\sin(\Psi - \theta)} \right| \quad (3)$$

In the equation, the phases (phases of pixels) of the image T to be separated and the main captured image R are respectively the phase θ and φ of the images (a low spatial resolution image without aliasing and a low spatial resolution image with aliasing) for the channels obtained in Step S42. The phase ψ of the image A can be obtained using a shift amount from θ corresponding to the reduction rate (ψ=θ+kπ, k is a coefficient determined by the reduction rate).

On the other hand, assuming that an image (complex number) of one channel among a plurality of channels is $T^i$, and an image (complex number) of one or more channels excluding $T^i$ from the plurality of channels is $T^o$, the image T is a composite of the images $T^i$ and $T^o$ of the plurality of channels. Assuming that the phases of the images ($T^i$, $T^o$) are α and β, the signal intensity (absolute value) of the image ($T^i$) can be represented by the following equation (4).

[Equation 4]

$$|Tn^i| = |Rn| \times \frac{\sin(\phi - \Psi)\sin(\theta - \beta)}{\sin(\theta - \Psi)\sin(\alpha - \beta)} \quad (4)$$

As described above, the phases α and β of the images $T^i$ and $T^o$ for each channel are respectively the phases of the low-resolution images for each channel obtained under the imaging conditions (a first pre-scan) that do not cause aliasing in Step S51. At this time, when obtaining amplification of the noise included in the main captured image (R) in the same manner as the equation (2), the following equation (5) is obtained.

[Equation 5]

$$(\delta T^i)^2 = \frac{m * \sin^2(\theta - \beta)}{\sin^2(\theta - \Psi)\sin^2(\alpha - \beta)} (\delta R)^2 \quad (5)$$

In the equation, m is a number obtained by adding 1 to the number n of channels of $T^o$ (that is, a total number of channels).

The image separation unit 230 determines a complex number z that minimizes the noise amplification represented by the equation (5) when the image of each channel is multiplied by a predetermined complex number z (S46). Then, each image is calculated by the equation (4) using the phase of the image multiplied by the complex number z (S47). That is, as shown in the following equations (6-1) to (6-4), the noise amplification evaluation unit 250 evaluates the noise amplification when performing a process of rotating the phases of an image $T^i$ ($=IU_i$) and an image $T^o$ ($=IU_j$) for each channel by the phase corresponding to the predetermined complex number z using the equation (5) as an evaluation function. Then, the complex number z ($z_i$ for each channel i) is determined so that the noise amplification is minimized.

[Equation 6]

$$\theta = \arg(\Sigma_{i=1}^{n+1} z_i \times IU_i) \quad (6\text{-}1)$$

$$\beta = \arg(\Sigma_{j \neq i}^{n} z_j \times IU_j) \quad (6\text{-}2)$$

$$\psi = \arg(\Sigma_{i=1}^{n+1} z_i \times A_i) \quad (6\text{-}3)$$

$$\alpha = \arg(z_i \times IU_i) \quad (6\text{-}4)$$

$A_i$ in the equation (6-3) is the low-resolution image with only aliasing, which is calculated by subtracting the low-resolution image ($IU_i$) obtained by the pre-scan in Step S41-1 from the low-resolution image including aliasing obtained by the pre-scan in Step S41-2.

The image separation unit 230 (noise amplification evaluation unit 250) performs an iterative operation using the equation (5) as the evaluation function, to determine the complex number $z_i$ to be multiplied to the images $T^i$ ($IU_i$) and $A_i$ of each channel so as to obtain the phases θ, β, ψ and α that minimize the noise amplification.

When the complex number z that minimizes the noise amplification is determined in this way, the phases θ, β, ψ and α obtained by the equations (6-1) to (6-4) from the images multiplied by the complex number z are applied to the equation (4), to calculate $|T^i|$ (S47). These steps are performed on the images of all the channels, to obtain the true image of each channel. Finally, the image ($T = \Sigma z_i \times IU_i$) from which the aliasing is eliminated is obtained using the true image $|T^i|$ obtained for each channel (S48). Thus, the true image can be separated while minimizing the noise amplification.

Similarly for the image A, the true image can be separated, that is, the aliasing can be unfolded using the same equation as the equation (4). Finally, as shown in FIG. 5A, the image in which the image T and the image A (A1, A2) are unfolded can be obtained.

As described above, according to the present embodiment, the image from which the aliasing is eliminated can be obtained by using the phase difference between the images without using sensitivity distribution of each channel. Further, the true image $T^i$ is calculated for the phase obtained from the low-resolution image of each channel, and the noise is minimized for the calculated images, so that the noise amplification which is difficult to be suppressed when using the sensitivity distribution of the channel can be suppressed.

<Modification of First Embodiment>

In the first embodiment, the low-resolution image of each channel is obtained by pre-scan, however, in general imaging, the low-resolution image for obtaining a sensitivity distribution is obtained for sensitivity correction separately from the main imaging. The image obtained by the pre-scan of the first embodiment may be replaced with such a low-resolution image. Further, the phase φ of the image with aliasing may not be obtained from the low-resolution image pre-scanned under the conditions that cause aliasing, but may be obtained by imaging only a central portion of the k-space at a normal sampling density in the main imaging and Fourier transforming the central portion.

In the first embodiment, a case where the pre-scan is performed prior to the main imaging has been described, however, their order does not matter.

Second Embodiment

In the present embodiment, the pulse sequence (SMS sequence: Simultaneous Multi Slice) using RF pulses that simultaneously excite the plurality of slices is employed as the pulse sequence. In the SMS pulse sequence, echo signals to be collected include signals from the plurality of slices, and the image obtained by Fourier transforming the k-space data including the echo signals is superimposed with the images of the plurality of slices. The image processing unit of the present embodiment separates the images of the slices from such a captured image.

Hereinafter, the present embodiment will be described focusing on differences from the first embodiment. First, the pulse sequence will be described with reference to FIGS. 7A to 7C. FIG. 7A shows a high-speed SE pulse sequence called TurboSpinEcho, FastSpinEcho or the like. After a 90° RF pulse for exciting a predetermined region of the subject, an inverted RF pulse (180° RF pulse) is continuously applied to the region. At that time, the echo signal is measured by applying a phase encoding gradient magnetic field between adjacent inversion RF pulses and applying a readout gradient magnetic field. By changing an application amount of the phase encoding gradient magnetic field applied for each echo, the data satisfying the k-space is collected by one or several excitations. Here, in the SMS pulse sequence, the RF pulse and the gradient magnetic field pulse applied at the same time are different from the normal high-speed SE pulse sequence for exciting a single slice (portions surrounded by square dashed lines in FIG. 7A). That is, in the pulse sequence, the RF pulse called a MB (multiband) pulse (FIG. 7B) or a PINS (Power Independent of Number of Slice) pulse (FIG. 7C) is used to simultaneously excite the plurality of slices. In the case of MB pulse, a slice selective gradient magnetic field having a constant strength is applied during the application, and in the case of the PINS pulse, a blip-shaped slice gradient magnetic field is applied. Further, a pulse combining the MB pulse and the PINS pulse, and the like are also known, and any pulse may be used.

The echo generated by such a pulse sequence is measured as a combination of signals from the plurality of slices excited. For example, as shown in FIGS. 8A to 8D, the image obtained by Fourier transforming the k-space data including the echoes is the image obtained by superimposing an image $S_1$ of a slice 1 and an image $S_2$ of a slice 2 when two slices are simultaneously excited. Note that each image is a composite of images of the plurality of channels.

The image separation unit 230 separates the image of each slice from the main captured image R on which the images of the plurality of slices are superimposed. Hereinafter, the process of the image separation unit 230 will be described by taking as an example a case of separating two slice images S1 and S2 shown in FIGS. 8A to 8D.

The two slice images $T_{s1}$, $T_{s2}$ and the main captured image R are represented by the complex numbers (vectors) as shown in FIG. 9A, when the signal at one point is shown on the complex plane. This figure is similar to a relationship between the true image T and the aliasing A shown in FIG. 3, and the vector sum of the complex numbers $S1_n$ and $S2_n$ is $R_n$ (The subscript "n" of $S1_n$ and $S2_n$ is the symbol for indicating that $S1_n$ and $S2_n$ are the pixels at each point included in the images $S_1$, $S_2$. The same applies hereinafter.). Further, as shown in FIG. 9B, the slice images $S_1$ and $S_2$ are the sum of images ($S1_n^i$ and $S1_n^o$) respectively obtained by the plurality of channels. In FIG. 9B, note that the slice image $S_1$ is shown as a representative, however, the same applies to the slice image $S_2$, which is the sum of images ($S2_n^i$, $S2_n^o$) of the plurality of channels. The phases (α, β) of the slice images $S1_n^i$ and $S1_n^o$ can be obtained by obtaining the low-resolution image by the pre-scan for each slice and Fourier transforming the central portion.

Figure 10:
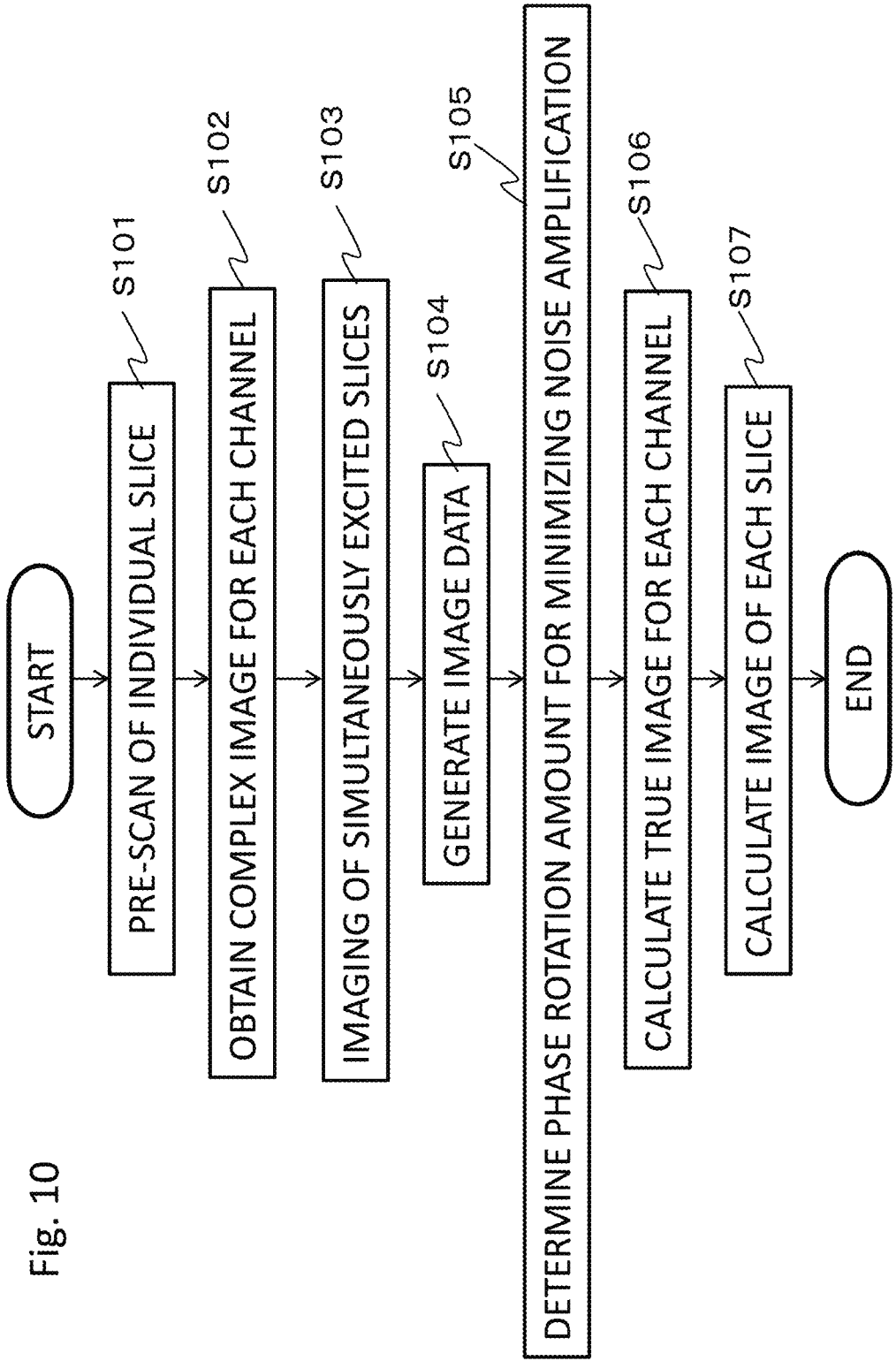
FIG. 10 is a flowchart showing processing by the image processing unit of the second embodiment.

Therefore, processing flow of the present embodiment is the same as that of the first embodiment. As shown in FIG. 10, each slice is pre-scanned (S101), the low-resolution image and the phase (α, β) of each channel for each slice are obtained (S102), the plurality of slices are simultaneously excited by the SMS pulse sequence, the main captured image is obtained (S103), and the image is separated (S104 to S107). In the image separation process, the noise amplification is minimized by optimizing the complex number to be multiplied to the image of each channel (S105). Then, the determined phases φ, ψ, α, β and the signal intensity and the phase θ of the main captured image R are applied to the same equarion as the equation (4), and the signal intensity of the slice image ($S1_n^i$, $S1_n^o$) is calculated for each channel (S106). At that time, specifically, when the slice image $S1_n^i$ is calculated, the equation (4) is the following equation (7).

[Equation 7]

$$|S1n^i| = |R| \times \frac{\sin(\phi - \Psi)\sin(\theta - \beta)}{\sin(\theta - \Psi)\sin(\alpha - \beta)} \quad (7)$$

When the slice image $S2_n^i$ is calculated, the equation (4) is the following equation (8).

[Equation 8]

$$|S2n^i| = |R| \times \frac{\sin(\phi - \theta)\sin(\Psi - \beta)}{\sin(\Psi - \theta)\sin(\alpha - \beta)} \quad (8)$$

Finally, the slice image of each channel is synthesized (S107), and the image of each slice can be obtained.

According to the present embodiment, with respect to the image obtained by the SMS pulse sequence, the images of the plurality of slices included in the image can be separated by using the phase of the low-resolution image. In that case, the noise of the captured image can be suppressed from being amplified by combining the images of the plurality of channels with a predetermined phase rotation.

In the present embodiment, a case of performing normal sampling has been described, but undersampling can also be performed in the present embodiment.

<Effects of Second Embodiment>

Figure 11A:
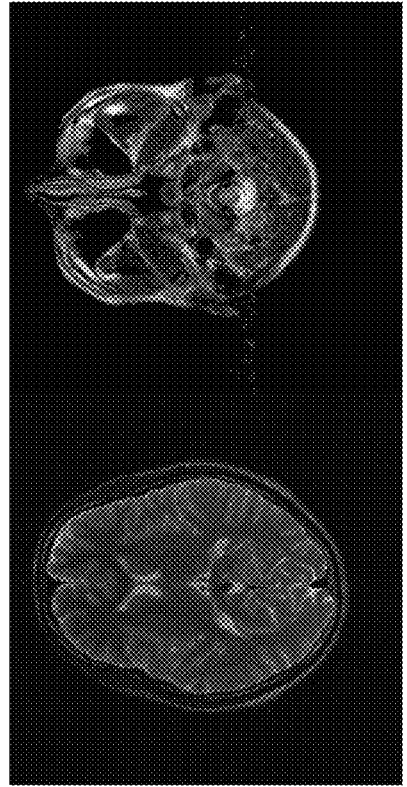
FIGS. 11A to 11D are views for explaining effects of the second embodiment.
Figure 11B:
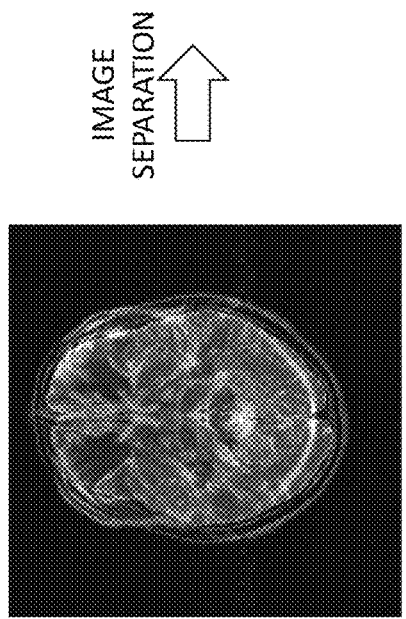
Figure 11C:
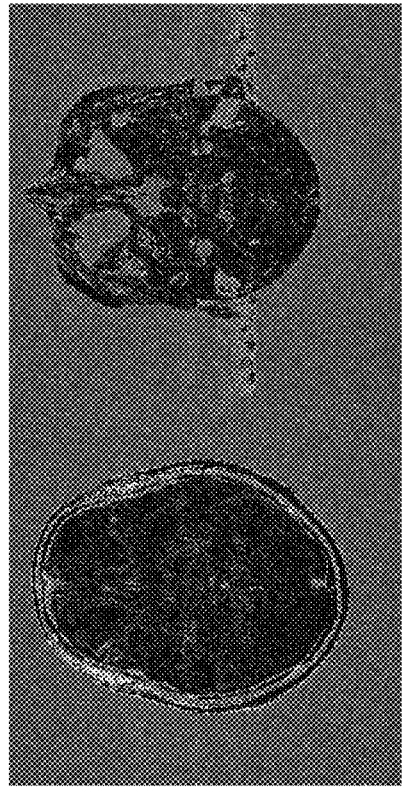
Figure 11D:
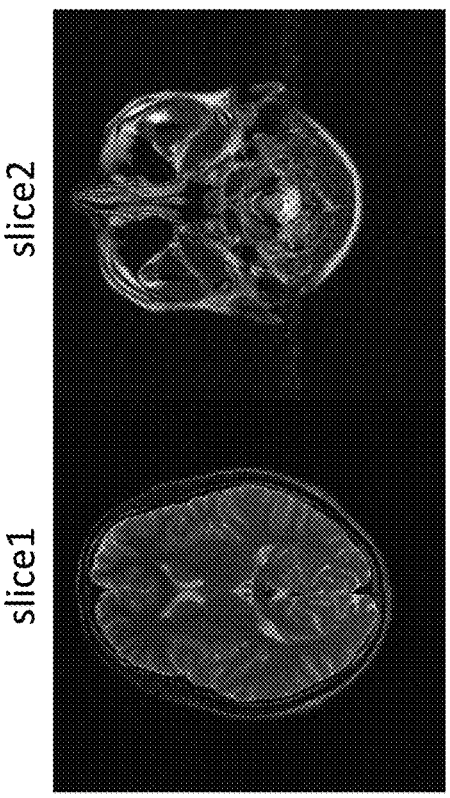

Results of separating each slice image by the method of the present embodiment using the image data of a head actually captured by the SMS pulse sequence was compared with the image obtained by imaging each slice alone. The results are shown in FIGS. 11A to 11D. FIG. 11A is an image obtained by imaging two slices by simultaneous excitation, FIG. 11B is an image obtained by exciting two slices independently, FIG. 11C is an image obtained by separating one slice from the image of FIG. 11A by the method of the present embodiment, and FIG. 11D is a difference between the image of one slice of FIG. 11B and the separated image of FIG. 11C.

As can be seen from a difference image shown in FIG. 11D, a signal value of a portion surrounded by a skull was almost zero, and the image separated by the method of the present embodiment (FIG. 11C) coincided well with the image captured alone (FIG. 11B).

Third Embodiment

The first embodiment is a case where the aliasing occurs in the image by undersampling at the predetermined reduction rate. However, even in normal imaging, if there is the subject outside the field of view, the signal from outside the field of view is mixed as aliasing. The present embodiment is an embodiment in which the method of the present invention is applied to elimination of such aliasing.

FIGS. 12A to 12D show a state of aliasing in the normal imaging. FIG. 12A shows a relationship between the subject and the field of view, and FIG. 12B shows the captured image R when the field of view is set as in FIG. 12A. As shown in the figure, in the captured image R, the aliasing A from outside the field of view is superimposed on the true image T. The relationship among the captured image R, the true image T, and the aliasing A is the same as the relationship among the images shown in FIG. 3.

Therefore, as in the first embodiment, the phases θ and ψ of the image T and the aliasing A obtained in the plurality of channels (FIG. 12C), and the phases α and β of the image T obtained in each channel (FIG. 12D) are optimized using the evaluation function of the equation (5) and then applied to the equation (4), so that the signal intensity of the true image for each channel can be obtained. Here, the phases θ, α and β can be obtained by performing low-resolution imaging in one pre-scan. However, in order to prevent aliasing in the pre-scan, the imaging is performed in a wider field of view than that of the main imaging. For example, the imaging is performed by doubling the field of view in the phase encoding direction, and the phase is obtained using a half image from a position in which the aliasing occurs if it is the field of view of the main imaging.

Obtaining the signal intensity of the true image by using the phase thus obtained, and optimizing the noise amplification by the complex number to be multiplied to the image of each channel, are the same as in the first embodiment.

According to the present embodiment, even when the imaging is performed with a small field of view set for a relatively large subject, the image without aliasing can be obtained without oversampling or the like, that is, by imaging for a relatively short time.

Although the embodiments of the present invention are described above, the present invention is not limited to the above embodiments, but modifications can be added appropriately. For example, in each embodiment, it is possible to add or delete elements that are not essential to an implementation of the present invention. Further, methods of the embodiments can be appropriately combined as long as there is no technical contradiction. Furthermore, performing the function of the image processing unit of each embodiment by an image processing apparatus different from the MRI apparatus, and performing by means other than software installed in the CPU, for example, performing by arithmetic means placed in a cloud, are all included in the present invention.

DESCRIPTION OF REFERENCE NUMERALS AND SIGNS

20: static magnetic field generating unit, 30: gradient magnetic field generating unit, 40: transmitting unit, 50: receiving unit, 60: sequencer, 70: CPU (control unit, image processing unit), 80: user interface unit, 100: imaging unit, 200: image processing unit, 210: reconstructing unit, 230: image separation unit, 300: control unit.

The invention claimed is:

1. A magnetic resonance imaging apparatus, comprising:
   an imager having a plurality of receiving coils and configured to collect nuclear magnetic resonance signals from a subject; and
   an image processor configured to reconstruct an image of the subject using the nuclear magnetic resonance signals collected by the imager, wherein
   the image processor comprises an image separator configured to separate a phase of a low-resolution image reconstructed from the nuclear magnetic resonance signals obtained by each of the plurality of receiving coils, and a phase of a main captured image that is reconstructed from the nuclear magnetic resonance signals obtained by the plurality of receiving coils, and superimposed with a plurality of images, to separate the plurality of images included in the main captured image,
   wherein the main captured image is an image, that is obtained by simultaneously collecting the nuclear magnetic resonance signals from a plurality of cross-sections of the subject by the imager, and superimposed with a plurality of cross-sectional images,
   wherein the image separator is configured to calculate a phase of each cross-sectional image from the phase of the low-resolution image obtained from each of the plurality of receiving coils for the plurality of cross-sections, and to use the phase of each calculated cross-sectional image, and a signal intensity and the phase of the main captured image, to calculate the signal intensity of each cross-sectional image.

2. The magnetic resonance imaging apparatus according to claim 1, wherein the low-resolution image is an image obtained by pre-scan by the imager.

3. The magnetic resonance imaging apparatus according to claim 1, wherein the low-resolution image is a reception sensitivity distribution image of the plurality of receiving coils.

4. The magnetic resonance imaging apparatus according to claim 1, wherein the main captured image is an image obtained by performing undersampled aquisition of data in a phase encoding direction by the imager.

5. The magnetic resonance imaging apparatus according to claim 1, wherein the main captured image is superimposed with an image in a field of view and an image aliased from outside the field of view.

6. The magnetic resonance imaging apparatus according to claim 5, wherein the image separator is configured to use a phase of the image in the field of view calculated from the phase of the low-resolution image obtained from each of the plurality of receiving coils, and a signal intensity and the phase of the main captured image, to calculate the signal intensity of the image in the field of view.

7. The magnetic resonance imaging apparatus according to claim 1, wherein the image processor further comprises a noise amplifier configured to permit evaluation of noise amplification during image separation by the image separator.

8. A magnetic resonance imaging apparatus, comprising:
an imager having a plurality of receiving coils and configured to collect nuclear magnetic resonance signals from a subject; and
an image processor configured to reconstruct an image of the subject using the nuclear magnetic resonance signals collected by the imager, wherein
the image processor comprises an image separator configured to separate a phase of a low-resolution image reconstructed from the nuclear magnetic resonance signals obtained by each of the plurality of receiving coils, and a phase of a main captured image that is reconstructed from the nuclear magnetic resonance signals obtained by the plurality of receiving coils, and superimposed with a plurality of images, to separate the plurality of images included in the main captured image,
wherein the image processor further comprises a noise amplifier configured to permit evaluation of noise amplification during image separation by the image separator, and
wherein the noise amplifier is configured to optimize the phase of the low-resolution image so as to minimize the noise amplification.

9. An image processing method for separating a true image from a measurement image obtained by magnetic resonance imaging and superimposed with a plurality of images including the true image, comprising:
a step (1) of calculating a phase of the true image using a low-resolution image; and
a step (2) of calculating a pixel value of the true image using a calculated phase of the true image and a phase and a pixel value of the measurement image, wherein the step (2) comprises a step of optimizing a phase of the low-resolution image so as to minimize noise amplification.

10. The image processing method according to claim 9, wherein
the measurement image is an image obtained by undersampled imaging using a plurality of receiving coils, and
in the step (1), the phase of the true image is calculated using a phase of the low-resolution image obtained for each of the plurality of receiving coils.

11. The image processing method according to claim 9, wherein
the measurement image is an image reconstructed from nuclear magnetic resonance signals simultaneously collected by simultaneously exciting a plurality of cross-sections of a subject, and
the low-resolution image is an image obtained by individually imaging the plurality of cross-sections.

* * * * *